(12) United States Patent
Chen et al.

(10) Patent No.: US 8,196,227 B2
(45) Date of Patent: Jun. 12, 2012

(54) GOGGLE WITH STRAP AND ASSEMBLY METHOD THEREOF

(75) Inventors: Wei-Sheng Chen, Tainan (TW);
Shu-Han Huang, Tainan (TW)

(73) Assignee: High Rainbow Ent. Co., Ltd., Tainan (TW)

( * ) Notice: Subject to any disclaimer, the term of this patent is extended or adjusted under 35 U.S.C. 154(b) by 930 days.

(21) Appl. No.: 12/189,894

(22) Filed: Aug. 12, 2008

(65) Prior Publication Data
US 2009/0260136 A1    Oct. 22, 2009

(30) Foreign Application Priority Data

Apr. 17, 2008 (TW) ................................ 97113892 A

(51) Int. Cl.
*A61F 9/02* (2006.01)
(52) U.S. Cl. ............................................................ 2/448
(58) Field of Classification Search ........ 2/448, 451–453; 351/111, 121
See application file for complete search history.

(56) References Cited

U.S. PATENT DOCUMENTS

| | | |
|---|---|---|
| 4,513,197 A | 4/1985 | Courvoisier et al. |
| 4,559,678 A | 12/1985 | Birkenstock |
| 4,689,838 A | 9/1987 | Angermann et al. |
| 4,924,557 A | 5/1990 | Heckerman et al. |
| 4,976,531 A | 12/1990 | Kahaney |
| 4,977,627 A | 12/1990 | Metcalfe et al. |
| 5,002,381 A | 3/1991 | Murrell |
| 5,181,280 A | 1/1993 | Zachry, Jr. |
| 5,189,447 A | 2/1993 | Oleson |
| 5,410,763 A * | 5/1995 | Bolle ................................ 2/436 |
| 5,617,588 A | 4/1997 | Canavan et al. |
| 5,628,072 A | 5/1997 | Haslbeck et al. |
| 5,650,866 A | 7/1997 | Haslbeck |
| 5,659,381 A | 8/1997 | Simioni |
| 5,706,527 A | 1/1998 | Kita et al. |
| 5,768,716 A | 6/1998 | Porsche |
| 5,809,580 A | 9/1998 | Arnette |
| 5,845,341 A | 12/1998 | Barthold et al. |
| 5,884,339 A | 3/1999 | Fukasawa |
| 5,918,351 A | 7/1999 | Chou |
| 5,959,714 A | 9/1999 | Chou |
| 6,047,410 A * | 4/2000 | Dondero ............................ 2/426 |
| 6,119,278 A | 9/2000 | Kawashima |
| 6,131,246 A | 10/2000 | Paulson et al. |
| 6,145,133 A | 11/2000 | Sato et al. |
| 6,149,268 A | 11/2000 | Hall et al. |
| 6,243,882 B1 | 6/2001 | Kawashima et al. |
| 6,276,794 B1 | 8/2001 | Chiang |
| 6,282,727 B1 * | 9/2001 | Lindahl ............................ 2/428 |
| 6,349,420 B1 | 2/2002 | Chiang |
| 6,349,421 B2 | 2/2002 | Fukasawa et al. |
| 6,477,717 B1 | 11/2002 | Winefordner et al. |

(Continued)

*Primary Examiner* — Katherine Moran
(74) *Attorney, Agent, or Firm* — Rosenberg, Klein & Lee

(57) ABSTRACT

A goggle and a strap assembly method thereof are provided. The goggle includes an eyeglass, a frame and at least one strap. The frame receives and secures the eyeglass therein and is bilaterally provided with a pair of engaging portions each having a through hole. The strap has at least one connecting portion and is passed through the through hole of a corresponding one of the engaging portions of the frame. The connecting portion of the strap is provided with a resisting portion which makes the connecting portion slightly larger than an opening of each of the through holes, so that the strap which is passed through the through hole of a corresponding one of the engaging portions can be securely attached to the frame.

8 Claims, 8 Drawing Sheets

U.S. PATENT DOCUMENTS

| | | |
|---|---|---|
| 6,575,570 B2 * | 6/2003 | Mauri ............................ 351/116 |
| 6,691,377 B2 | 2/2004 | Pan |
| 6,691,378 B1 | 2/2004 | Chou |
| 6,896,366 B2 | 5/2005 | Rice et al. |
| 6,928,663 B1 | 8/2005 | Tappeiner |
| 7,003,811 B2 | 2/2006 | Canavan |
| 7,159,978 B2 | 1/2007 | Skuro |
| 7,162,750 B2 | 1/2007 | Canavan |
| 2002/0010959 A1 | 1/2002 | Fukasawa et al. |
| 2005/0128426 A1 | 6/2005 | Shiue |
| 2005/0132478 A1 | 6/2005 | Canavan |
| 2005/0254001 A1 | 11/2005 | Winningham |
| 2005/0268386 A1 * | 12/2005 | Oishi et al. ....................... 2/448 |
| 2006/0143808 A1 | 7/2006 | Canavan |
| 2006/0181674 A1 | 8/2006 | Skuro |
| 2008/0047051 A1 | 2/2008 | Winningham |
| 2008/0111966 A1 | 5/2008 | Chiang |

* cited by examiner

# GOGGLE WITH STRAP AND ASSEMBLY METHOD THEREOF

BACKGROUND OF THE INVENTION

1. Technical Field

The present invention relates to a goggle and a strap or temple, and assembly methods thereof. More particularly, the present invention relates to a method for coupling a strap having a resisting portion or a temple having an interlocking portion to a goggle.

2. Description of Related Art

Over the decades, industrial development has greatly enhanced our living standards but also resulted in all kinds of industrial accidents or disasters. Factory workers or teachers and students at practice workshops suffer from various injuries and occupational diseases due to negligence to industrial safety and hygiene. As a more serious consequence, instances of public nuisance arise, including air pollution, water pollution and countless other disastrous incidents. Therefore, industrial safety and hygiene is indeed an important issue that must not be overlooked. Standards and specifications for all kinds of safety equipment have been stipulated in related laws and regulations to demand public attention to such protective gears. Among the various items of safety equipment are safety glasses, safety muffs, earplugs, respirators, protective goggles and dark-colored glasses.

Taiwan Patent No. M298134 discloses a pair of goggles having a fastening device. The goggles comprise an outer cover 10, a strap 20 and a transparent eyeglass 30. The outer cover 10 is a perforated frame having a rear end designed to cover fittingly around a user's eyes. The outer cover 10 is bilaterally provided with outwardly protruding blocks 14, each formed with an engaging through groove 15. The transparent eyeglass 30 is mounted at a front end of the outer cover 10. The goggles are characterized in that a buckle 21 is provided at each of two ends of the strap 20 for engaging with a corresponding one of the engaging through grooves 15 on the outer cover 10. Each of the buckles 21 is formed with at least one fastening hole 22 for the strap 20 to pass through and be secured thereby. It is not necessary to assembly the strap 20 to the outer cover 10 with the buckles 21 until the goggles are to be used. However, the strap 20 and the buckles 21 are assembled to the goggles merely by passing the strap 20 through the fastening holes 22 on the buckles 21 and engaging the buckles 21 with the engaging through grooves 15 on the outer cover 10, wherein there is no special clamping design between the strap 20 and the buckles 21. As a result, the strap 20 tends to get loose relative to the fastening holes 22.

In addition, Taiwan Patent No. M295260 discloses a goggles assembly characterized in that an eyeglass 1 of the goggles has two ends, each pivotally provided with a connecting block 2 having a through slot 21, and each of the connecting blocks 2 has a sidewall formed with an insertion hole 22. The goggles assembly further comprises an insertion tab 3 which is formed with a raised insertion block 31 and can be inserted into the through slot 21 of a corresponding one of the connecting blocks 2, so that the insertion block 31 is inserted into the insertion hole 22 of a corresponding one of the connecting blocks 2. The insertion tab 3 further has a rear end assembled with a retaining element 4, such as a temple or a strap, to be worn by a user. The retaining element 4 is connected to the through slot 21 of a corresponding one of the connecting blocks 2 by the insertion tab 3 and secured in place by the insertion block 31 inserted in the insertion hole 22. Thus, the retaining element 4 is assembled to the goggles assembly by engagement on only one side of the retaining element 4. If the insertion block 31 is damaged or deformed due to an external stress or other external factors, the retaining element 4 tends to get loose relative to the eyeglass 1 and needs to be replaced entirely, thereby increasing the usage cost.

BRIEF SUMMARY OF THE INVENTION

In order to solve the aforementioned problems, a primary objective of the present invention is to provide a goggle formed by putting together an eyeglass, a frame and a strap or a temple, so as to lower the complexity of the production process.

Another primary object of the present invention is to provide a goggle which can be assembled in a simpler way to lower the cost of time and manpower for assembly and disassembly.

A further primary object of the present invention is to provide a goggle comprising a strap, wherein the strap is provided with a resisting portion formed by inserting a buckle through a strap loop, so as to provide a higher component replaceability and a better engagement effect.

Still another primary object of the present invention is to provide a goggle comprising a temple, wherein the temple has an interlocking portion, and an interlocking pillar of the interlocking portion is made of a resilient material to provide a better interlocking effect.

Yet another primary object of the present invention is to provide a goggle and a strap or temple assembly method thereof, wherein a simpler assembly process is employed to lower the cost of time and manpower for assembly and disassembly.

To achieve these objectives, the present invention provides a goggle and a strap or temple, and an assembly method thereof. The goggle comprises an eyeglass, a frame and at least one strap. The frame receives and secures the eyeglass therein and is bilaterally provided with a pair of engaging portions, each having a through hole. The strap has at least one connecting portion and can be passed through the through hole of a corresponding one of the engaging portions of the frame. The connecting portion of the strap has a resisting portion which makes the connecting portion slightly larger than an opening of each of the through holes, so that the strap which is passed through the through hole of a corresponding one of the engaging portions can be securely attached to the frame.

The present invention also provides another goggle and a strap or temple, and an assembly method thereof. The goggle comprises an eyeglass, a frame and at least one temple. The frame receives and secures the eyeglass therein and is bilaterally provided with at least one pair of side holes. The temple has at least one interlocking portion for engaging with a corresponding one of the side holes of the frame, thereby connecting the temple to the frame.

Since the goggle disclosed in the present invention is formed by putting together the eyeglass, the frame and the strap or the temple, which is a relatively simple assembly method, the cost of time and manpower for assembly and disassembly can be greatly reduced. Furthermore, as the goggle is formed by assembly, if a component is damaged due to wear and tear, a user only has to replace the damaged component individually, particularly one of the components for coupling the strap or the temple to the frame, such as the resisting portion of the strap or the interlocking portion of the temple. Since there is no need to discard the goggle entirely, unnecessary waste can be avoided.

BRIEF DESCRIPTION OF THE SEVERAL VIEWS OF THE DRAWINGS

The invention as well as a preferred mode of use, further objectives and advantages thereof will best be understood by reference to the following detailed description of illustrative embodiments when read in conjunction with the accompanying drawings, wherein.

DETAILED DESCRIPTION OF THE INVENTION

The present invention discloses a goggle and a strap or temple, and an assembly method thereof. Since the production or processing procedures of goggles employed in the present invention can be achieved by existing techniques, a detailed description of such procedures will be omitted herein. Besides, the drawings referred to herein are not drawn according to actual dimensions because they are intended to demonstrate features of the present invention only schematically.

Figure 1:
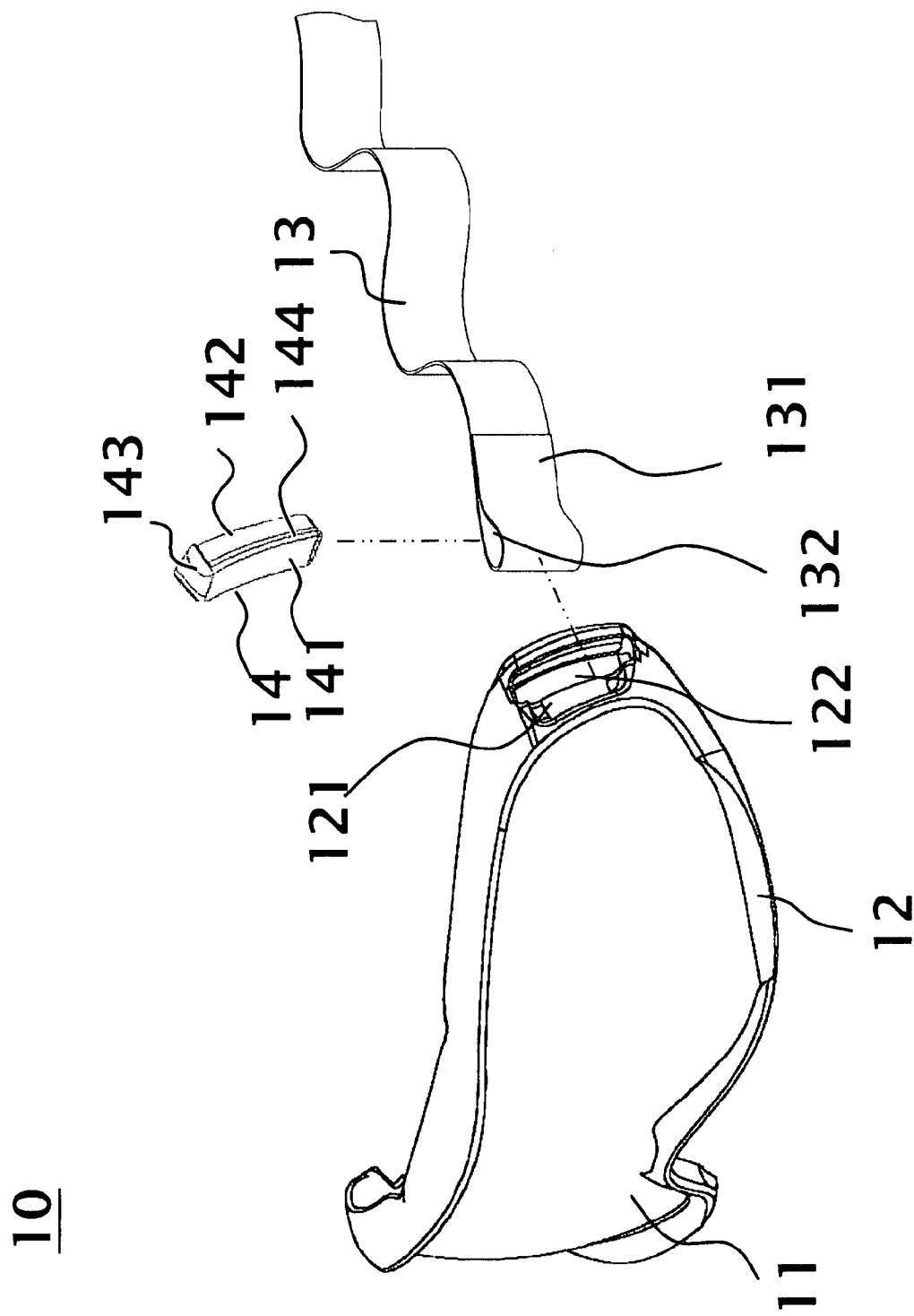
FIG. 1 is a schematic view of a goggle according to an embodiment of the present invention.

FIG. 1 shows a preferred embodiment of a goggle according to the present invention, wherein a goggle 10 comprises an eyeglass 11, a frame 12 and at least one strap 13. The frame 12 receives and secures the eyeglass 11 therein and is bilaterally provided with a pair of engaging portions 121 each having a through hole 122. The frame 12 can generally be formed of a rigid material. The strap 13 has two opposite ends each formed as a connecting portion 131 for engaging with a corresponding one of the two engaging portions 121 of the frame 12. The strap 13 also has a strap loop 132 formed at each of the connecting portions 131 thereof. In addition, the strap 13 can generally be formed of a resilient material. The strap 13 is passed through the through hole 122 of each of the engaging portions 121 of the frame 12. Each of the connecting portions 131 of the strap 13 has a resisting portion 133 which makes the connecting portion 131 slightly larger than an opening of a corresponding one of the through holes 122, so that the strap 13 can be securely attached to the frame 12.

Figure 2A:
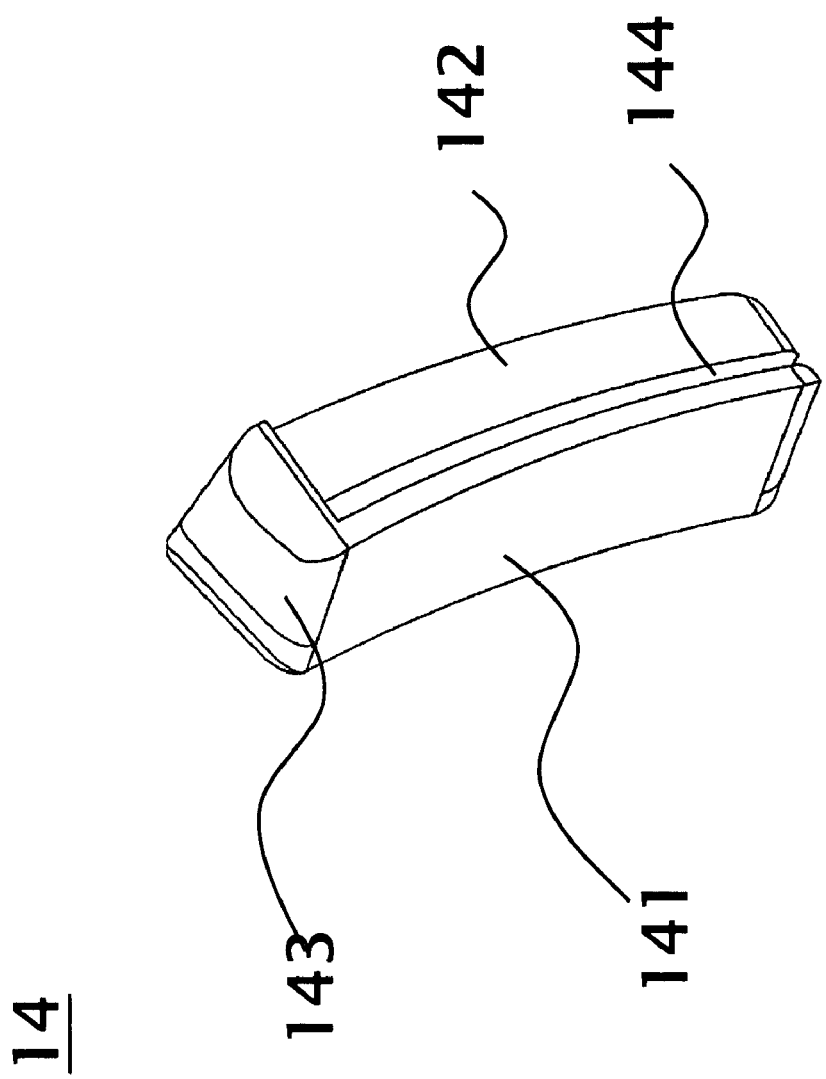
FIGS. 2A and 2B are schematic views of a buckle according to an embodiment of the present invention.
Figure 2B:
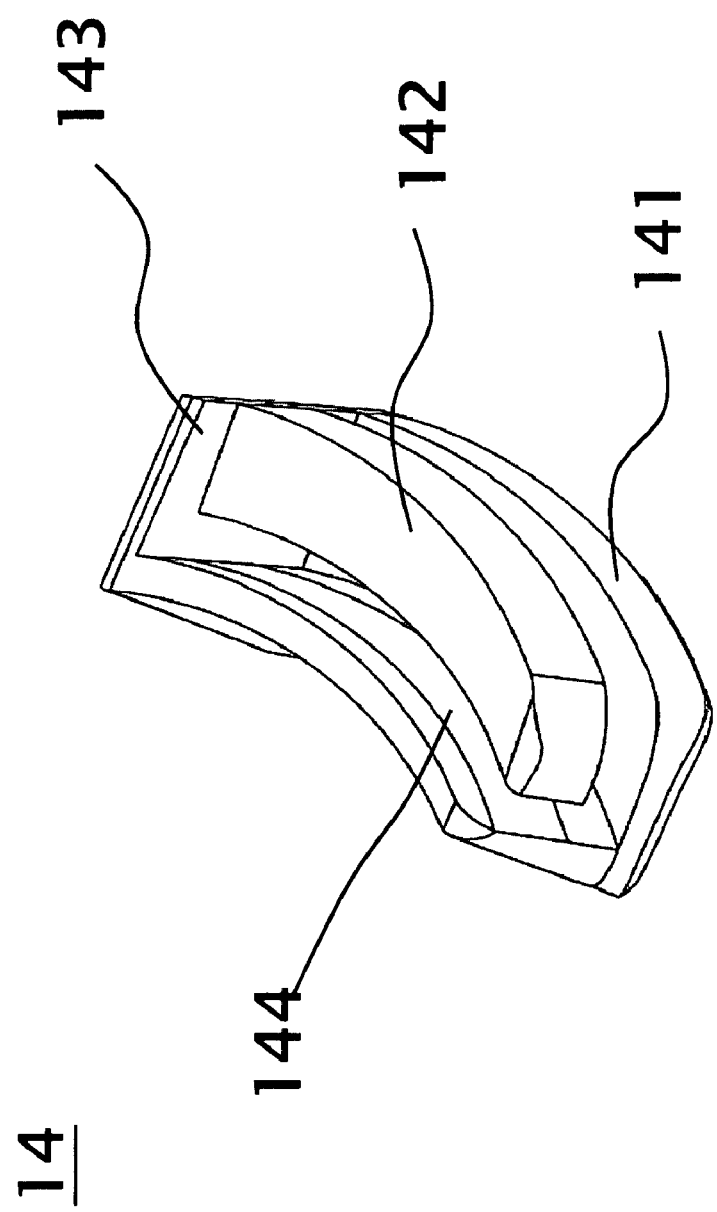
Figure 3:
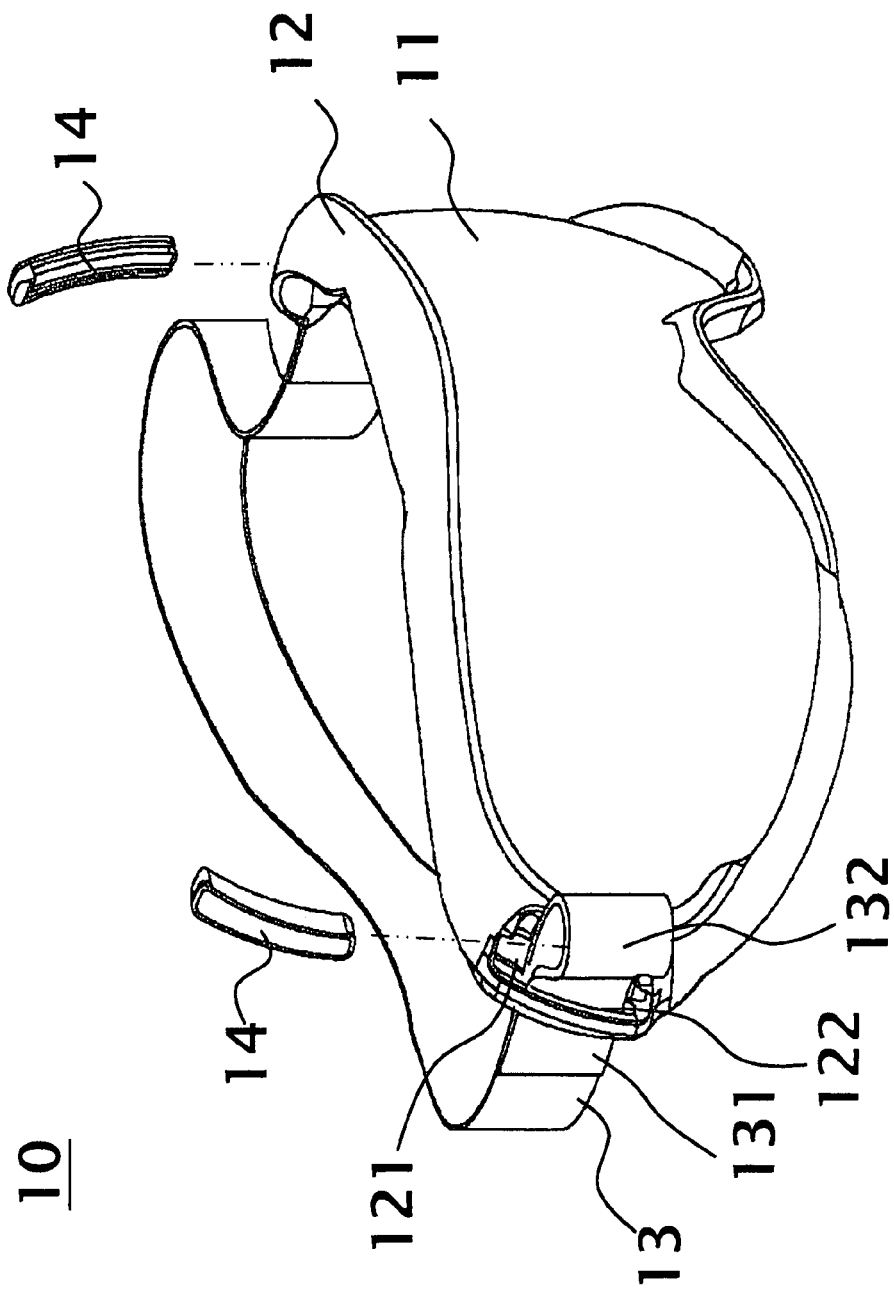
FIGS. 3 and 4 are schematic views showing a method for coupling a strap to a goggle according to an embodiment of the present invention.

As shown in FIG. 3, the resisting portion 133 is formed by inserting a buckle 14 into the strap loop 132. Referring to FIGS. 2A and 2B, the buckle 14 has a resisting plate 141 and a resisting pillar 142 connected by a bridge 143 therebetween, thereby forming a buckle groove 144 between the resisting pillar 142 and the resisting plate 141. The resisting plate 141 is generally L-shaped, so that the buckle groove 144 is also generally L-shaped. The buckle 14 can generally be formed of a rigid material or a resilient material and is integrally formed as one piece.

Figure 4:
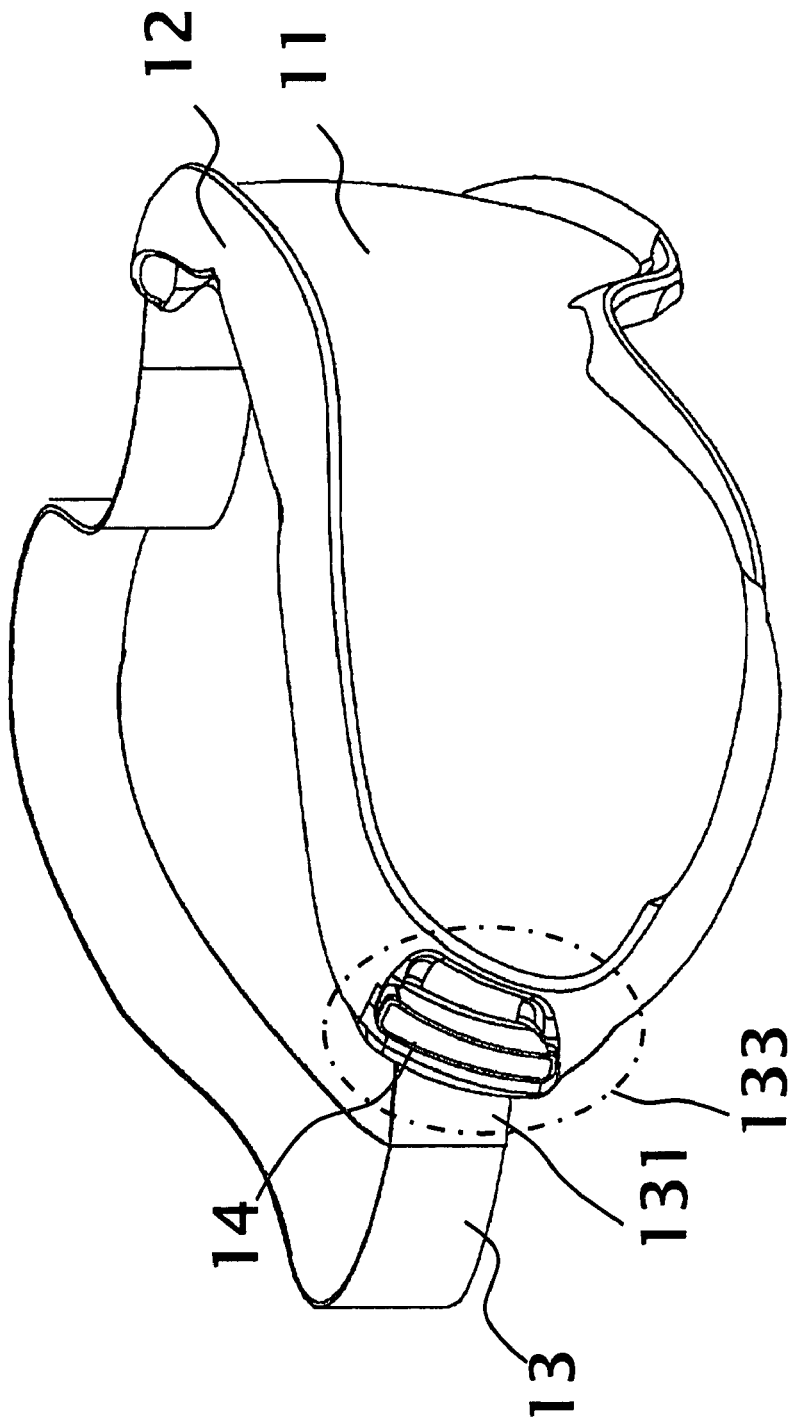

FIG. 1 also shows schematically a preferred embodiment of a method for coupling a strap to a goggle according to the present invention. The method comprises the steps of providing a frame 12 for receiving and securing an eyeglass 11 therein, wherein the frame 12 is bilaterally provided with at least one pair of engaging portions 121, and each of the engaging portions 121 has a through hole 122; providing at least one strap 13, wherein the strap 13 has a pair of connecting portions 131 formed with a strap loop 132; and providing a buckle 14, wherein the buckle 14 has at least one resisting plate 141 and a resisting pillar 142. Referring to FIG. 3, the method further comprises the steps of passing the strap 13 through the through hole 122 of a corresponding one of the engaging portions 121 of the frame 12, so that the strap loop 132 is exposed outside the through hole 122; inserting the resisting pillar 142 of the buckle 14 into the strap loop 132, thereby securing the buckle 14 to the connecting portion 131 of the strap 13 to form a resisting portion 133, wherein the resisting plate 141 of the resisting portion 133 makes the connecting portion 131 of the strap 13 slightly larger than an opening of the through hole 122 of a corresponding one of the engaging portions 121. Referring to FIG. 4, the method further comprises the step of pulling the strap 13 in a direction away from the resisting portion 133, so that the connecting portion 131 of the strap 13 is engaged with the corresponding one of the engaging portions 121 of the frame 12.

Figure 5:
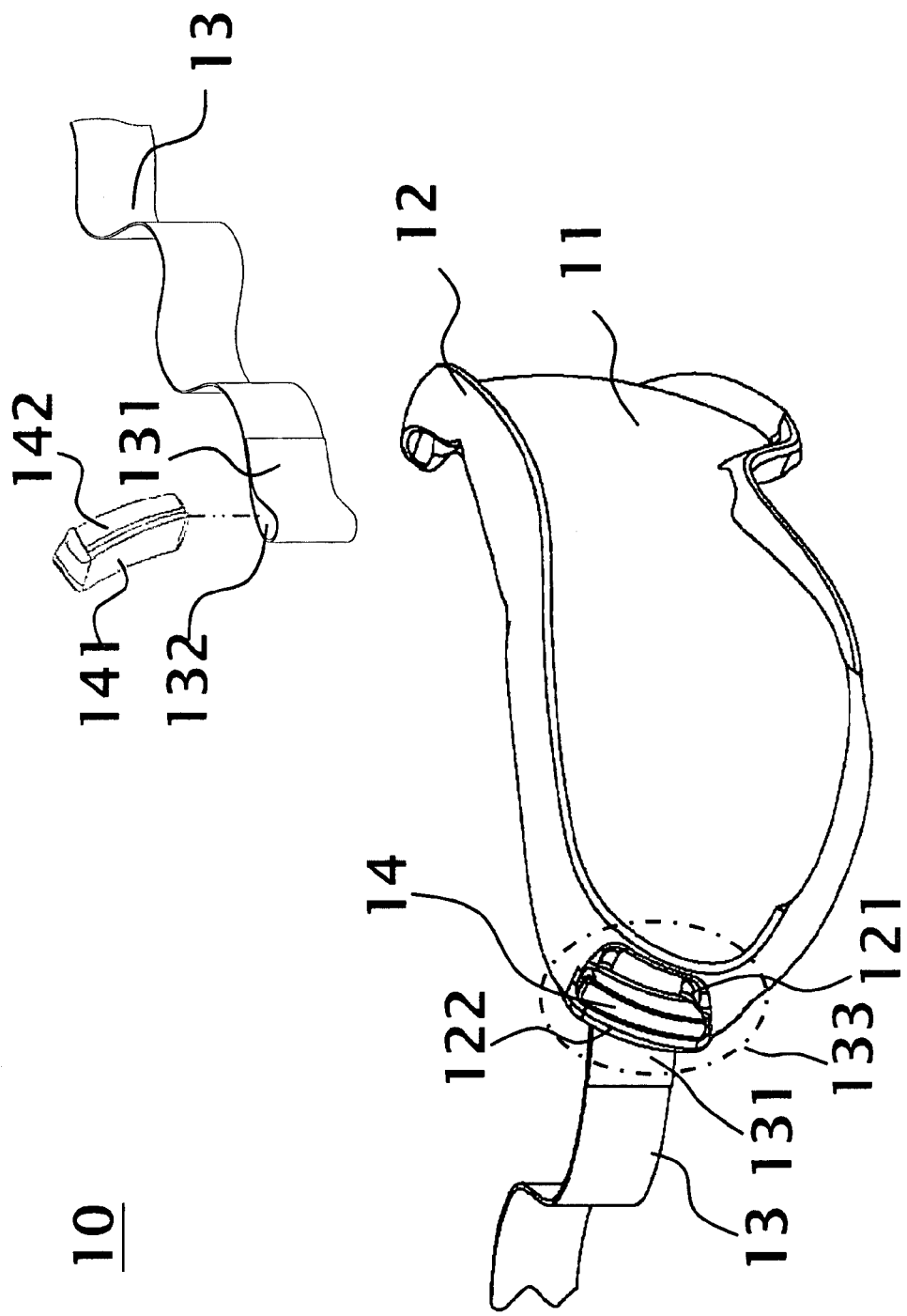
FIGS. 5 to 7 are schematic views showings goggles and methods for coupling a strap or a temple to the goggles according to further embodiments of the present invention.

FIG. 5 shows another preferred embodiment of a goggle according to the present invention, wherein a goggle 10 comprises an eyeglass 11, a frame 12 and at least one pair of straps 13. The frame 12 receives and secures the eyeglass 11 therein and is bilaterally provided with at least one pair of engaging portions 121, wherein each of the engaging portions 121 has a through hole 122, and the frame 12 can generally be formed of a rigid material. Each of the straps 13 has one and only one connecting portion 131. The connecting portions 131 of the two straps 13 can be engaged respectively with the two oppositely disposed engaging portions 121 of the frame 12. In addition, each of the straps 13 also has a strap loop 132 formed at the connecting portion 131 thereof. The straps 13 can generally be formed of a resilient material. Each of the straps 13 is passed through the through hole 122 of a corresponding one of the engaging portions 121 of the frame 12. The connecting portion 131 of each strap 13 has a resisting portion 133 which makes the connecting portion 131 slightly larger than an opening of a corresponding one of the through holes 122, so that each strap 13 can be securely attached to the frame 12.

As shown in FIG. 3, the resisting portion 133 is formed by inserting a buckle 14 into the strap loop 132. Referring to FIGS. 2A and 2B, the buckle 14 has a resisting plate 141 and a resisting pillar 142 connected by a bridge 143 therebetween, thereby forming a buckle groove 144 between the resisting pillar 142 and the resisting plate 141. The resisting plate 141 is generally L-shaped, so that the buckle groove 144 is also generally L-shaped. The buckle 14 can generally be formed of a rigid material or a resilient material and is integrally formed as one piece.

FIG. 5 also shows schematically another preferred embodiment of a method for coupling a strap to a goggle according to the present invention. The method comprises the steps of providing a frame 12 for receiving and securing an eyeglass 11 therein, wherein the frame 12 is bilaterally provided with at least one pair of engaging portions 121, and each of the engaging portions 121 has a through hole 122; providing at least one pair of straps 13, wherein each of the straps 13 has a connecting portion 131 formed with a strap loop 132; providing a buckle 14, wherein the buckle 14 has at least one resisting plate 141 and a resisting pillar 142; inserting the resisting pillar 142 of the buckle 14 into the strap loop 132 of a corresponding one of the straps 13, thereby securing the buckle 14 to the connecting portion 131 of the strap 13, wherein the resisting plate 141 forms a resisting portion 133 which makes the connecting portion 131 of the strap 13 slightly larger than an opening of the through hole 122 of a corresponding one of the engaging portions 121; passing the straps 13 through the through holes 122 of the corresponding engaging portions 121 of the frame 12, respectively; and pulling the straps 13 in a direction away from the corresponding resisting portions 133, so that the connecting portions 131 of the straps 13 are engaged with the corresponding engaging portions 121 of the frame 12, respectively.

Figure 6:
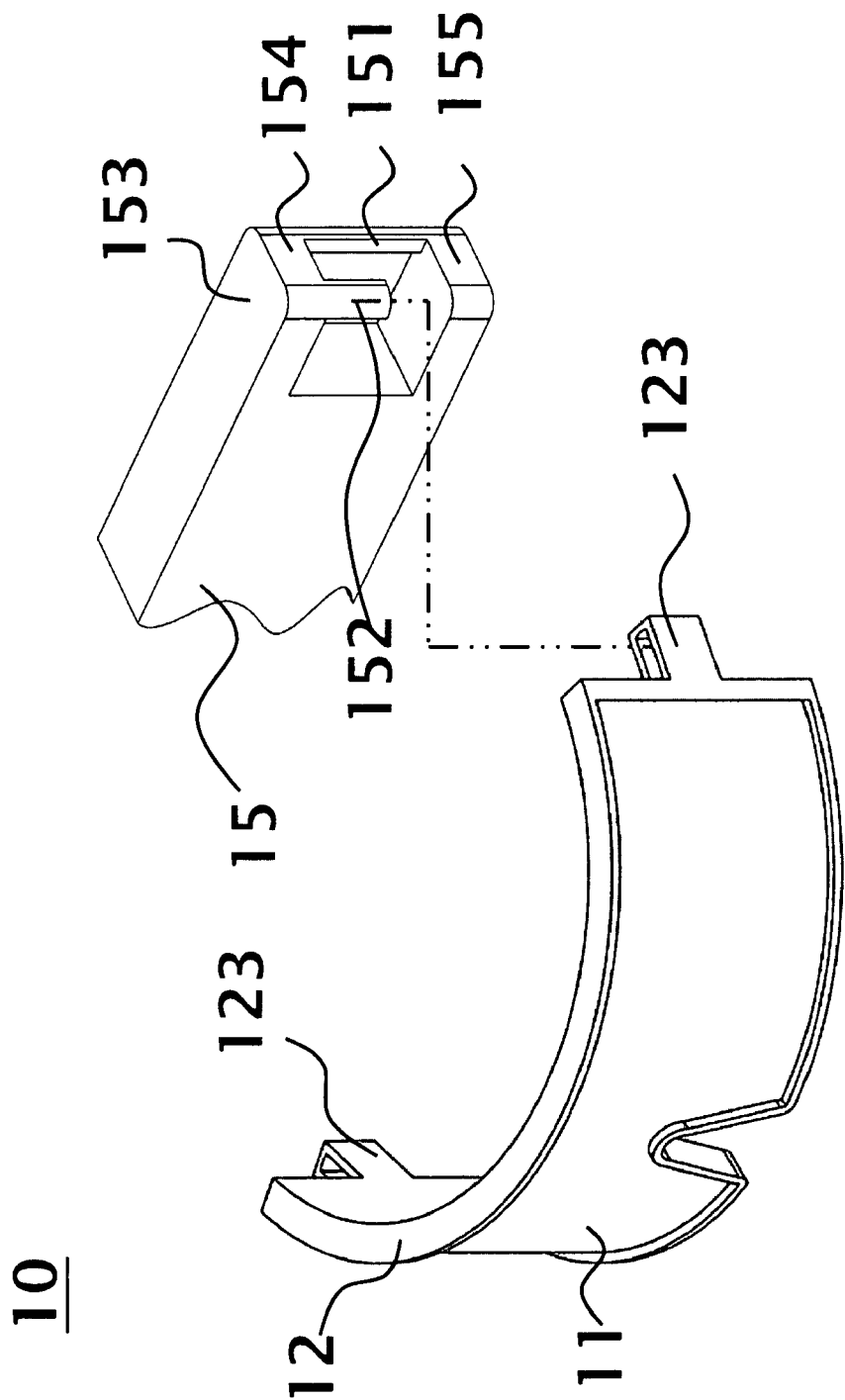

FIG. 6 shows yet another preferred embodiment of a goggle according to the present invention, wherein a goggle 10 comprises an eyeglass 11, a frame 12 and at least one temple 15. The frame 12 receives and secures the eyeglass 11 therein and is bilaterally provided with at least one pair of side holes 123. The temple 15 has at least one interlocking portion 151 for engaging with a corresponding one of the side holes 123 of the frame 12, thereby connecting the temple 15 to the frame 12.

As shown in FIG. 6, the interlocking portion 151 has an interlocking pillar 152 to be inserted in a corresponding one of the side holes 123, and an withstanding portion 153 allowing the frame 12 and the temple 15 to have a fixed relative position, wherein the interlocking portion 151 can be integrally formed as one piece. The withstanding portion 153 has a first withstanding member 154 and a second withstanding member 155. The interlocking pillar 152 extends from the first withstanding member 154 so that a gap is formed between the interlocking pillar 152 and the second withstanding member 155. The interlocking pillar 152 can be a basic cylinder or a rectangular column formed with a lead angle. When the interlocking pillar 152 is a rectangular column formed with a lead angle, the rectangular shape of the interlocking pillar 152 generates an interfering action that allows firmer rotation. The interlocking pillar 152 can generally be formed of a resilient material, such as a PC material or a nylon material, so that the interlocking pillar 152 can be easily inserted into a corresponding one of the side holes 123 but cannot be removed therefrom as easily as inserted thereinto, thus providing a better interlocking effect.

FIG. 6 also shows schematically a preferred embodiment of a method for coupling a temple to a goggle according to the present invention. The method comprises the steps of providing a frame 12 for receiving and securing an eyeglass 11 therein, wherein the frame 12 is bilaterally provided with at least one pair of side holes 123; providing at least one temple 15 having at least one interlocking portion 151, wherein the interlocking portion 151 has an interlocking pillar 152 to be inserted in a corresponding one of the side holes 123, and at least one withstanding portion 153 allowing the frame 12 and the temple 15 to have a fixed relative position, in which the withstanding portion 153 has a first withstanding member 154 and a second withstanding member 155, and the interlocking pillar 152 extends from the first withstanding member 154, thereby forming a gap between the interlocking pillar 152 and the second withstanding member 155; and placing the second withstanding member 155 of the temple 15 against an end of a corresponding one of the side holes 123 and inserting the interlocking pillar 152 into the side hole 123, so that the first withstanding member 154 abuts against the other end of the side hole 123. Thus, the interlocking portion 151 is engaged with the side hole 123 and the temple 15 is thereby connected to the frame 12.

Figure 7:
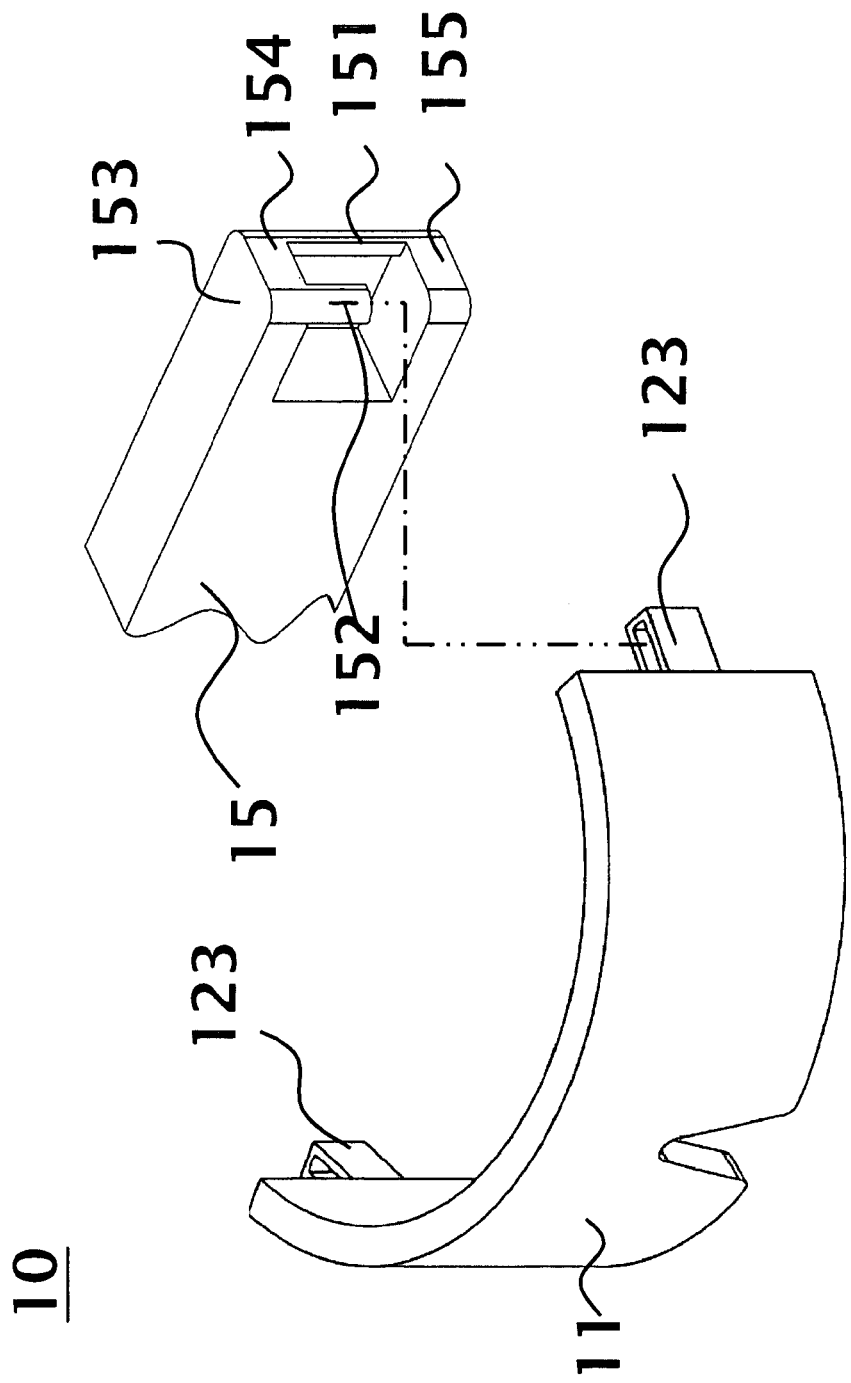

FIG. 7 shows still another preferred embodiment of a goggle according to the present invention, wherein a goggle 10 comprises an eyeglass 11 and at least one temple 15. The eyeglass 11 is bilaterally provided with at least one pair of side holes 123. The temple 15 has at least one interlocking portion 151 for engaging with a corresponding one of the side holes 123 of the eyeglass 11, thereby connecting the temple 15 to the eyeglass 11.

The interlocking portion 151 has an interlocking pillar 152 to be inserted in a corresponding one of the side holes 123, and an withstanding portion 153 allowing the eyeglass 11 and the temple 15 to have a fixed relative position, wherein the interlocking portion 151 can be integrally formed as one piece. The withstanding portion 153 has a first withstanding member 154 and a second withstanding member 155. The interlocking pillar 152 extends from the first withstanding member 154 so that a gap is formed between the interlocking pillar 152 and the second withstanding member 155. The interlocking pillar 152 can be a basic cylinder or a rectangular column formed with a lead angle. When the interlocking pillar 152 is a rectangular column formed with a lead angle, the rectangular shape of the interlocking pillar 152 generates an interfering action that allows firmer rotation. The interlocking pillar 152 can generally be formed of a resilient material, such as a PC material or a nylon material, so that the interlocking pillar 152 can be easily inserted into a corresponding one of the side holes 123 but cannot be removed therefrom as easily as inserted thereinto, thus providing a better interlocking effect.

FIG. 7 also shows schematically another preferred embodiment of a method for coupling a temple to a goggle according to the present invention. The method comprises the steps of providing an eyeglass 11 bilaterally provided with at least one pair of side holes 123; providing at least one temple 15 having at least one interlocking portion 151, wherein the interlocking portion 151 has an interlocking pillar 152 to be inserted in a corresponding one of the side holes 123, and at least one withstanding portion 153 allowing the eyeglass 11 and the temple 15 to have a fixed relative position, in which the withstanding portion 153 has a first withstanding member 154 and a second withstanding member 155, and the interlocking pillar 152 extends from the first withstanding member 154, thereby forming a gap between the interlocking pillar 152 and the second withstanding member 155; and placing the second withstanding member 155 of the temple 15 against an end of a corresponding one of the side holes 123 and inserting the interlocking pillar 152 into the side hole 123, so that the first withstanding member 154 abuts against the other end of the side hole 123. Thus, the interlocking portion 151 is engaged with the side hole 123 and the temple 15 is thereby connected to the eyeglass 11.

The present invention provides an improvement over the prior part. More specifically, the present invention provides a goggle comprising an eyeglass, a frame and a strap or a temple assembled together in a simpler way so as to reduce significantly the cost of time and manpower for assembly and disassembly. Furthermore, as the goggle is formed by assembly, if a component is damaged due to wear and tear, a user only has to replace the damaged component, particularly one of the components for coupling the strap or the temple to the frame, such as the resisting portion of the strap or the interlocking portion of the temple. Since there is no need to discard the goggle entirely, unnecessary waste can be avoided.

The present invention has been described with reference to preferred embodiments thereof, which are provided for illustrative purposes only and not intended to limit the scope of the present invention. Moreover, as the contents disclosed herein should be readily understood and can be implemented by a person skilled in the art, all equivalent changes or modifications which do not depart from the spirit of the present invention should be encompassed by the appended claims.

What is claimed is:

1. A goggle, comprising:
   an eyeglass;
   a frame for receiving and securing said eyeglass therein, wherein said frame is bilaterally provided with at least one pair of engaging portions, and each of said engaging portions has a through hole; and
   at least one strap having at least one connecting portion and passed through said through hole of a corresponding one of said engaging portions of said frame, wherein said connecting portion has a loop formed in said strap thereat; and
   at least one buckle engaged with said strap loop and being larger than said through hole of said corresponding engaging portion to securely attach said at least one strap to said frame, said buckle having at least one resisting plate and at least one resisting pillar inserted into said strap loop.

2. The goggle according to claim 1, wherein said strap has two opposite ends each formed with a corresponding connecting portion, and said connecting portions are respectively engaged with said two opposite engaging portions of said frame.

3. The goggle according to claim 1, comprising at least one pair of the straps, wherein each of said straps has one and only one said connecting portion, and said connecting portions of the two straps are each engaged with a corresponding one of the two opposite engaging portions of said frame.

4. The goggle according to claim 1, wherein said buckle further comprises a bridge connecting said resisting pillar with said resisting plate, so as to form a buckle groove between said resisting pillar and said resisting plate.

5. The goggle according to claim 1, wherein said resisting plate is generally L-shaped.

6. The goggle according to claim 1, wherein said buckle is generally formed of one of a rigid material and a resilient material.

7. The goggle according to claim 1, wherein said buckle is integrally formed as one piece.

8. A method for coupling a strap to a goggle comprising steps of:
   providing a frame for receiving and securing an eyeglass therein, wherein said frame is bilaterally provided with at least one pair of engaging portions, and each of said engaging portions has a through hole;
   providing at least one strap, wherein said strap has at least one connecting portion formed with a strap loop;
   providing a buckle having at least one resisting plate and a resisting pillar;
   passing the strap through said through hole of a corresponding one of said engaging portions of said frame, so that said strap loop is exposed outside said through hole;
   inserting said resisting pillar of said buckle into said strap loop of said connecting portion, thereby securing said buckle to said connecting portion of said strap, wherein said resisting plate forms a resisting portion which makes said connecting portion of said strap slightly larger than an opening of said through hole of a corresponding one of said engaging portions; and
   pulling said strap in a direction away from said resisting portion, so that said connecting portion of said strap is engaged with said corresponding one of said engaging portions of said frame.

* * * * *